US006387115B1

(12) United States Patent
Smolka et al.

(10) Patent No.: US 6,387,115 B1
(45) Date of Patent: May 14, 2002

(54) PHOTODYNAMIC CYLINDRICAL LAMP WITH ASYMMETRICALLY LOCATED ELECTRODES AND ITS USE

(75) Inventors: Ernst Smolka, Aschaffenburg; Jörn Jahnke, Hanau; Ullrich Berger, Breitenborn, all of (DE)

(73) Assignee: Heraeus Noblelight GmbH, Hanau (DE)

( * ) Notice: Subject to any disclaimer, the term of this patent is extended or adjusted under 35 U.S.C. 154(b) by 0 days.

(21) Appl. No.: 09/653,459

(22) Filed: Aug. 31, 2000

(30) Foreign Application Priority Data

Jul. 27, 2000 (DE) ........................................ 100 37 032

(51) Int. Cl.[7] ................................................. A61N 5/00

(52) U.S. Cl. ......................... 607/88; 313/620; 313/623; 313/573

(58) Field of Search .............................. 607/88, 90, 91; 250/504 R; 313/326, 491, 493, 573, 574, 620, 623, 631

(56) References Cited

U.S. PATENT DOCUMENTS

| | | | | |
|---|---|---|---|---|
| 3,753,019 A | | 8/1973 | Hellman | |
| 4,103,175 A | * | 7/1978 | Levin | 250/504 R |
| 4,287,554 A | * | 9/1981 | Wolff | 362/218 |
| 4,469,102 A | * | 9/1984 | Fish | 607/91 |
| 4,524,299 A | * | 6/1985 | Preston, III | 313/487 |
| 4,645,969 A | * | 2/1987 | Hoffman | 313/487 |
| 4,843,279 A | * | 6/1989 | Rattray et al. | 313/487 |
| 4,967,090 A | * | 10/1990 | Schlitt | 250/504 R |
| 4,984,571 A | * | 1/1991 | Springer, Jr. et al. | 607/94 |
| 5,565,685 A | * | 10/1996 | Czako et al. | 250/504 R |
| 5,957,959 A | * | 9/1999 | Rissmaney et al. | 607/88 |
| 6,147,448 A | * | 11/2000 | Huang | 313/491 |

FOREIGN PATENT DOCUMENTS

| | | |
|---|---|---|
| EP | 0 807 959 A2 | 11/1997 |
| FR | 2 334 197 | 1/1977 |
| JP | 54082867 | 7/1979 |
| JP | 62108447 | 5/1987 |
| JP | 05041197 | 2/1993 |

* cited by examiner

*Primary Examiner*—Michael Peffley
(74) *Attorney, Agent, or Firm*—Oblon, Spivak, McClelland, Maier & Neustadt, P.C.

(57) ABSTRACT

A high-capacity UV radiation apparatus, especially a high-capacity mercury low-pressure tube, for vertical applications, including a discharge chamber that is formed by a cylindrical flask made of UV-transmissive glass and that contains a filling gas, a first or a second electrode, and electrical connections leading to the outside, with an electrode holder being arranged in the area of each flask. One electrode holder is considerably longer than the other electrode holder. The temperature of the cold spot in the dead electrode space is therefore reduced on the longer electrode holder, with the steam pressure or efficiency curve of the radiation apparatus being optimized with a vertical arrangement of the radiation apparatus with the long electrode holder in the upper position. In order to ensure correct assembly, the apparatus contains a marking on at least one flask end, which provides information about the length of the respective electrode holder.

5 Claims, 1 Drawing Sheet

PHOTODYNAMIC CYLINDRICAL LAMP WITH ASYMMETRICALLY LOCATED ELECTRODES AND ITS USE

FIELD OF THE INVENTION

The invention relates to a high-capacity UV radiation apparatus, especially a high-capacity mercury low-pressure tube, for vertical applications, with a discharge chamber that is formed by cylindrical flask made of UV-transmissive glass and closed on both ends and that contains a filling gas, with a first or a second electrode, which includes electrical connections leading to the outside, with an electrode holder being arranged in this chamber in the area of the flask end. The invention furthermore relates to the usage of the high-capacity UV radiation apparatus.

BACKGROUND OF THE INVENTION

High-capacity UV radiation apparatuses, also called high-capacity tanning tubes, as they are employed for example for the treatment of or for tanning the human body through ultraviolet radiation, have a symmetrical design regarding the length of the electrodes and electrode holders. This means that on both ends of the discharge chamber formed by a quartz flask one electrode, respectively, with an electrode holder is arranged, which has the same length as the electrode holder on the opposite end of the quartz flask. With increased efficiency and reduced temperatures of the so-called cold spots in the dead electrode space (area behind the electrodes towards the flask end) in mind, radiation apparatuses with so-called long holder electrodes were developed, which however have a shorter life than such with short holder electrodes. Conversely, it was found that although high-capacity UV radiation apparatuses with symmetrical short holder electrodes have a long life, they do not display an optimal steam pressure curve in the area of the electrodes. Generally, both types (short holder electrodes, long holder electrodes) of the high-performance UV radiation apparatus are employed in horizontal applications, for example in tanning beds or tanning chambers, in lighting equipment in the form of fluorescent tubes or in degerminating systems.

During the vertical operation of familiar high-capacity UV radiation apparatuses, the above-mentioned disadvantages become particularly clear since additionally occurring convection reinforces the unbalanced radiation capacity throughout the length of the high-capacity UV radiation apparatus.

The invention at issue is therefore based on the task of making a high-capacity UV radiation apparatus for vertical operation available that overcomes the above-mentioned disadvantages of the state of the art and guarantees stable high-capacity operation even with a tightly packed arrangement of the individual radiation apparatuses while ensuring correct assembly of the radiation apparatus without additional efforts.

The above task is resolved with the invention due to the fact that the length of the electrode holder of the first electrode deviates from the length of the electrode holder of the second electrode by a certain amount, with the flask end with the longer or with the shorter electrode holder containing a marking.

The invented high-capacity radiation apparatuses excels through the fact that one electrode holder is considerably longer than the other electrode holder. The temperature of the cold spot in the dead electrode space is therefore reduced on the longer electrode holder, with the steam pressure or efficiency curve of the radiation apparatus being optimized with a vertical arrangement of the radiation apparatus with the long electrode holder in the upper position. In order to ensure correct assembly, the invented radiation apparatus contains a marking on at least one flask end, which provides information about the length of the respective electrode holder. For example a direction arrow and/or the word "up" can indicate that the long electrode holder is located at that end and that this end of the high-capacity UV radiation apparatus should be installed on the top.

With regard to the optimization of the efficiency curve of the invented radiation apparatus in vertical operation, it has proven beneficial if the length of the first electrode holder of the first electrode deviates from the length of the electrode holder of the second electrode by at least 5 millimeters. A difference in length of the electrode holders that has been found to be effective is about 10 mm for radiation apparatuses that are about 2 meters long.

Furthermore it is beneficial if the UV-transmissive glass of the flask consists of borosilicate glass or silica glass, depending on the wall thickness of the flask and the emitted wave range of the radiation apparatus. For a wave range larger than 280 nm and a low wall thickness of the flask (about 0.1 to 0.3 mm), borosilicate glass can be used as the UV transmissive glass. Applications for this are generally in lighting technology, where luminous matter, which enables absorption of radiation in the desired wave range, is preferably applied to the interior wall of the glass flask for the conversion of radiation into visible light. For the usage of the invented radiation apparatus in degerminating systems on the other hand a higher flask wall thickness is required for lower wave ranges so that due to the high, consistent transmission silica glass is the chosen material for the flask of the radiation apparatus.

It is useful to employ radiation in the wave ranges between 170 nm and 1000 nm for the invented high-capacity UW radiation apparatus. Certain wave ranges are preferred for certain application purposes. For example the preferred UV spectrum for tanning purposes is between 280 nm and 400 nm, for fluorescent tubes it is between 380 nm and 780 nm, and for radiation apparatuses that are used in degerminating systems it is in the range between 170 nm and 300 nm.

Furthermore, it is useful if the electrical power consumption of the high-capacity UV radiation apparatus does not exceed 300 watts, since this way the heating of the high-capacity radiation apparatus during operation is limited. This goes hand in hand with reduced power dissipation and thus increased efficiency.

Particularly beneficial application areas of the invented high-capacity UV radiation apparatus are tanning, degerminating or lighting devices, where it is mounted vertically.

A particularly preferred application of the high-capacity UV radiation apparatus is a tanning device in the form of a tanning booth. The tanning booth comprises a basically cylindrical housing as a cabin in which the person can stand up and on whose interior wall the invented high-capacity radiation apparatuses are arranged vertically in such a way that the flask end with the short electrode holder is located in the bottom area of the tanning booth and the one with the long electrode holder in the upper area of the tanning booth. The high-capacity radiation apparatus is equipped with a marking on at least one end of its silica glass flask for correct and simple assembly. Of course, reverse assembly (short electrode holder on top) of the invented high-capacity UV radiation apparatus is possible for certain isolated cases as well.

SUMMARY OF THE INVENTION

The invention relates to a high-capacity UV radiation apparatus, especially a high-capacity mercury low-pressure tube, for vertical applications, with a discharge chamber that is formed by a cylindrical flask made of UV-transmissive glass and that contains a filling gas, with a first or a second electrode, which includes electrical connections leading to the outside, with an electrode holder being arranged in the area of each flask end. The invention furthermore relates to the usage of the high-capacity UV radiation apparatus.

Generally, high-capacity UV radiation apparatuses are employed horizontally. With regard to increasing efficiency and reducing the temperature of so-called cold spots in the dead electrode space, radiation apparatuses with long holder electrodes were developed, which however have a shorter life than those with short holder electrodes. Conversely, high-capacity UV radiation apparatuses with symmetrical short holder electrodes have a longer life, but do not display an optimal steam pressure curve in the area of the electrodes. During vertical operation of familiar high-capacity UV radiation apparatuses, the above-mentioned disadvantages become very clear through additionally occurring convection. Based on the invention, the suggestion is made to allow the length of the electrode holder of the first electrode to deviate from the length of the electrode holder of the second electrode by a certain amount, with the flask end with the longer or with the shorter electrode holder being equipped with a marking. Such radiation apparatuses ensure stable high-capacity operation and simple and correct assembly even in tightly packed arrangements.

BRIEF DESCRIPTION OF THE DRAWINGS

The invention is explained in greater detail in the following by means of a drawing.

DESCRIPTION OF A PREFERRED EMBODIMENT

Figure 1:
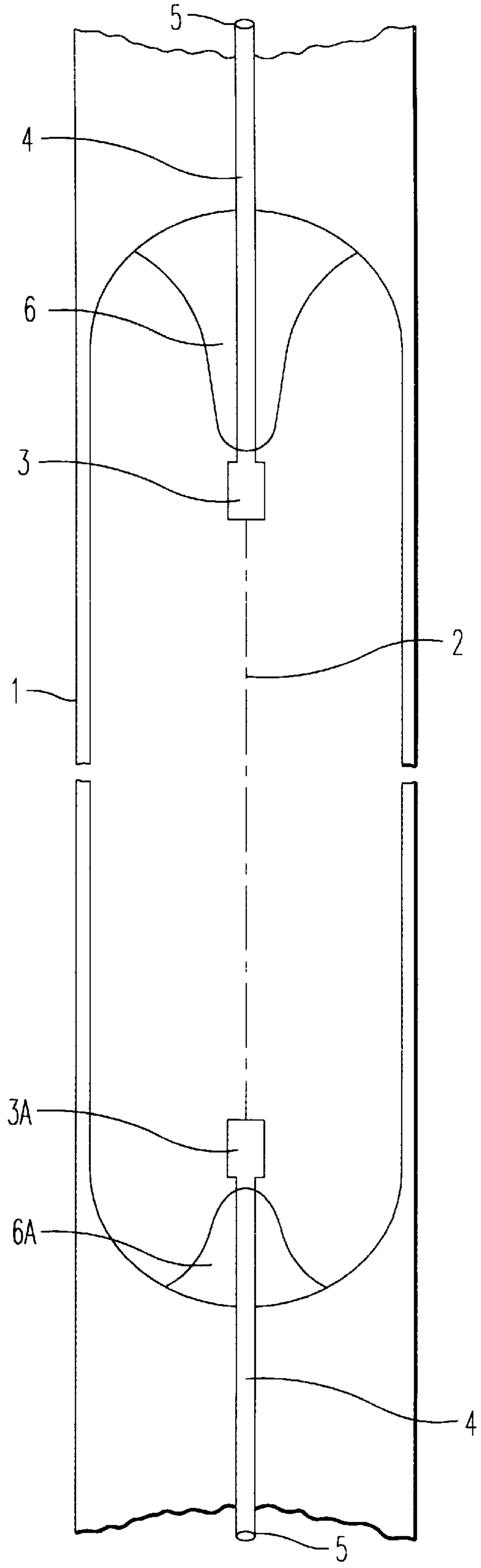
FIG. 1 shows the single FIGURE of one version of the invented high-capacity radiation apparatus in diagrammatic view.

In accordance with FIG. 1, the interior of the lamp flask 1 consisting of silica glass has a cylindrical design, where the electrodes 3, 3*a* are arranged symmetrically on opposite sides along the axis 2 of the lamp flask 1. The overall length of the high-capacity UV radiation apparatus is 2 m. This example shows a high-capacity mercury low-pressure tube for applications in tanning booths. The electrodes 3, 3*a*, respectively, are connected with the outer connection 5 via power lines 4, which are embedded in a vacuum-tight manner in the lamp flask 1 consisting of silica glass. The electrodes 3, 3*a*, respectively, are equipped with an electrode holder 6, 6*a* facing the interior of the lamp flask 1, with the holder taking on a bell-type shape. The electrode holder 6 differs in its length from the electrode holder 6*a* by about 15 mm. On the outer wall of the lamp flask 1, a marking 7 in the form of a direction arrow (not shown in the figure) pointing in the direction of the outer connection is applied in the area of the electrode holder 6.

What is claimed is:

1. A high-capacity UV radiation apparatus, especially a high-capacity mercury low-pressure tube, for vertical applications, comprising:

a discharge chamber that is formed by a cylindrical flask made of UV-transmissive glass and closed on a first and a second end, wherein the discharge chamber contains a filling gas;

a first electrode disposed in a first electrode holder, which includes electrical connections leading to the outside, wherein the first electrode holder is located in an area of the first end of the flask; and a second electrode disposed in a second electrode holder, which includes electrical connections leading to the outside, wherein the second electrode holder is located in an area of the second end of the flask, wherein there is a measurable difference between a length of the first electrode holder and a length of the second electrode holder; and the first end or the second end of the flask being equipped with a marking.

2. The high-capacity UV radiation apparatus in accordance with claim 1, wherein the difference between the length of the first electrode holder and the length of the second electrode holder is at least 5 millimmeters.

3. The high-capacity UV radiation apparatus in accordance with claim 1, wherein the UV-transmissive glass is silica glass or borosilicate glass, depending on a wall thickness of the flask and a range of emitted wave of the radiation apparatus.

4. The high-capacity UV radiation apparatus in accordance with claims 1, 2 or 3, wherein the emitted radiation in a wavelength range of 170 to 1000 nm.

5. The high-capacity UV radiation apparatus in accordance with claim 4, wherein an electrical power consumption of the radiation apparatus is 300 watts or less.

* * * * *

UNITED STATES PATENT AND TRADEMARK OFFICE

CERTIFICATE OF CORRECTION

PATENT NO. : 6,387,115 B1
DATED : May 14, 2002
INVENTOR(S) : Ernst Smolka et al.

It is certified that error appears in the above-identified patent and that said Letters Patent is hereby corrected as shown below:

<u>Column 2,</u>
Line 37, change “UW radiation apparatus” to -- UV radiation apparatus --.

Signed and Sealed this

Thirty-first Day of December, 2002

JAMES E. ROGAN
*Director of the United States Patent and Trademark Office*